US012649945B2

(12) United States Patent　　　　(10) Patent No.:　　US 12,649,945 B2

Wickenberg et al.　　　　　　　　　(45) Date of Patent:　　*Jun. 9, 2026

(54) DETECTION OF MYCOBACTERIUM ON GROWTH MEDIA

(71) Applicants:Leah Wickenberg, Reno, NV (US);
Avneet K. Chhabra, Sparks, NV (US);
William F. McCoy, Reno, NV (US)

(72) Inventors: Leah Wickenberg, Reno, NV (US);
Avneet K. Chhabra, Sparks, NV (US);
William F. McCoy, Reno, NV (US)

(73) Assignee: Phigenics, LLC

( * ) Notice: Subject to any disclaimer, the term of this
patent is extended or adjusted under 35
U.S.C. 154(b) by 188 days.

This patent is subject to a terminal dis-
claimer.

(21) Appl. No.: 18/389,115

(22) Filed: Nov. 13, 2023

(65)　　　　　Prior Publication Data

US 2024/0132930 A1　　　Apr. 25, 2024

Related U.S. Application Data

(63) Continuation-in-part of application No. 17/172,726,
filed on Feb. 10, 2021, now Pat. No. 11,814,668.

(60) Provisional application No. 62/976,631, filed on Feb.
14, 2020.

(51) Int. Cl.
*C12Q 1/04*　　　　(2006.01)
(52) U.S. Cl.
CPC ............... *C12Q 1/04* (2013.01); *C12Q 1/045*
(2013.01)

(58) Field of Classification Search
None
See application file for complete search history.

(56)　　　　　References Cited

U.S. PATENT DOCUMENTS 11,814,668 B2 * 11/2023 Wickenberg ............. C12Q 1/04

OTHER PUBLICATIONS

McBride et al. "Evaluation of commercials blood containing media
for cultivation of *Mycobacterium haemophilusn*". Am J Clin Pathol
1992, 98, pp. 282-286.*
Radomski et al. Applied and Environmental Microbiology, 2010,
vol. 76, No. 11, pp. 3514-3520.*
Kondo et al. "Examinations of disinfectant assay systems on acid-
fast bacteria". Dermatology (Basel), 1997, vol. 195, No. Suppl. 2,
p. 148.*
Remel's Technical Manual of Microbiological Media, Description
of Casman Agar with 5% sheep blood. 2010, p. 1.*

* cited by examiner

*Primary Examiner* — Vera Afremova

(74) *Attorney, Agent, or Firm* — Ian Burns; Darren
Gardner; American Law, LTD

(57)　　　　　ABSTRACT

To determine the presence of *Mycobacterium* in an environ-
ment, a sample from the environment can be plated onto a
growth medium that is selective for *Mycobacterium*. Prior to
plating, the sample may be treated with a compound con-
taining sodium dodecyl sulfate containing glycine hydro-
chloride. Plating may occur immediately after the addition
of the compound or after a standing period. The agar based
growth medium can include a high concentration of crystal
violet, in excess of 0.5 µg/ml. *Mycobacterium* colonies will
generally appear white while other colonies will generally
appear stained purple or another color.

3 Claims, 4 Drawing Sheets

DETECTION OF MYCOBACTERIUM ON GROWTH MEDIA

CROSS REFERENCE TO RELATED APPLICATIONS

This application is a Continuation-in-part of U.S. patent application Ser. No. 17/172,726 filed 10 Feb. 2021, issued on 14 Nov. 2023 as U.S. Pat. No. 11,814,668, which claims priority to U.S. provisional patent application Ser. No. 62/976,631, filed 14 Feb. 2020. The contents of each of these applications is incorporated herein by reference.

FIELD OF THE INVENTION

The present invention relates to methods and compositions used in detecting bacteria.

BACKGROUND OF THE INVENTION

The Problem of *Mycobacterium*

*Mycobacterium* is a genus of acid-fast bacteria that encompasses approximately 200 species. This genus includes serious human pathogens such as the causative agents of tuberculosis and leprosy. While *Mycobacterium tuberculosis* and *Mycobacterium leprae* are more globally known and studied, another category of *Mycobacterium*, called non-tuberculous *Mycobacterium* (NTM), is emerging as a significant threat to public health. In some places, NTM infections cause a greater disease burden than tuberculosis.

NTM exist ubiquitously in most environments and have recently gained interest as a frequent cause of infection. NTM infections most commonly lead to pulmonary disease; other possible infections include lymphadenitis, skin infections, and disseminated disease. Importantly, immunocompromised individuals are far more susceptible to NTM than most individuals. Treatment for mycobacterial infections are often lengthy, expensive, and extremely harsh on the patient, therefore early detection and prevention are imperative as control measures.

NTM infections have not been shown to transmit person to person. Most infections thus far have been traced to the environment, predominantly from water through aerosol inhalation and aspiration. Alarmingly, many clinical cases have been traced to potable water systems, including municipal drinking water and hospital water.

Limitations of Growth Media and Current Diagnostics for *Mycobacterium*

Currently, the most commonly used media for the growth of *Mycobacterium* are Lowenstein-Jensen (LJ) media, R2A media, and Middlebrook media (including 7H9, 7H10, and 7H11). Culture plates remain the "gold standard" for identifying mycobacterial infections or contamination (ASTM, 2015). Since water and/or clinical samples from which *Mycobacterium* are isolated are frequently contaminated with other bacteria, and since *Mycobacterium* grow much slower than average bacteria, isolating them from samples can be difficult as current media offer little differentiation and selection for them (Radomski et al., 2010).

Diagnostics for *Mycobacterium*, especially NTM, are severely limited, expensive, and time-consuming. The standard *Mycobacterium* diagnostics include spread-plating a sample onto a limited nutrient agar plate, often with antibacterial ingredients to inhibit non-mycobacterial growth and allow for easier selection of the bacteria.

Current decontamination or pretreatment steps utilized to isolate *Mycobacterium* from overgrown samples involve harsh reagents and complicated procedures that can significantly inhibit the growth of multiple species of *Mycobacterium*. For example, Cetylpyridinium chloride (CPC) is widely used to decontaminate water samples to aid in the isolation of *Mycobacterium*. Recent studies show that sample pretreatment of CPC can significantly reduce the growth of clinically important *Mycobacterium* species such as *M. abscessus*. Another pretreatment used on samples is the reagent N-acetyl-1-cysteine-sodium hydroxide (NALC-NaOH). Pretreatment with this reagent requires a complex protocol (i.e. time-consuming incubations and centrifugations) that can take up to over an hour per sample.

What is required are improved techniques and products for detecting and differentiating *Mycobacterium*.

SUMMARY OF ONE EMBODIMENT OF THE INVENTION

Advantages of One or More Embodiments of the Present Invention

The various embodiments of the present invention may, but do not necessarily, achieve one or more of the following advantages:

the ability to differentiate *Mycobacterium* from other bacteria;

the ability to detect non-tuberculous *Mycobacterium* (NTM);

provide a novel growth medium for *Mycobacterium;* provide a pretreatment method for enhancing positive detection of *Mycobacterium;* provide a more cost-effective method for detection of *Mycobacterium.*

These and other advantages may be realized by reference to the remaining portions of the specification, claims, and abstract.

BRIEF DESCRIPTION OF ONE EMBODIMENT OF THE PRESENT INVENTION

In one aspect of the present invention, there is provided a method for determining the presence of *Mycobacterium* in a sample. The method may include obtaining a sample from the environment. A portion of the sample may be plated onto a growth medium and incubated for an incubation period. After the incubation period, an inspection of one or more bacterial growth colonies may determine the presence of *Mycobacterium* in the environment. The growth medium may comprise an agar based growth medium comprising agar, one or more amino acid and nitrogenous supplementation elements, one or more trace elements and vitamins, one or more carbon sources, one or more neutralizing agents, and crystal violet. The crystal violet may be provided in an amount in excess of 0.5 μg/ml.

In one embodiment, the crystal violet may be provided in an amount in excess of 1.0 μg/ml. In one embodiment, the crystal violet may be provided in an amount in excess of 1.5 μg/ml. In one embodiment, the crystal violet may be provided in an amount in excess of 2.0 μg/ml.

In one embodiment, the sample may be treated with sodium dodecyl sulfate containing glycine hydrochloride prior to plating.

In one aspect, there is provided a method for determining the presence of *Mycobacterium* in a sample. The method may include obtaining a sample from the environment. The sample may be treated with a compound containing sodium dodecyl sulfate and glycine hydrochloride and then plated onto a growing medium. After an incubation period, an inspection of one or more bacterial growth colonies on the growth medium may determine the presence of *Mycobacterium* in the environment.

In one embodiment, the growing medium may be an agar based growth medium comprising agar, one or more amino acid and nitrogenous supplementation elements, one or more trace elements and vitamins, one or more carbon sources, one or more neutralizing agents and crystal violet for differentiating non-*Mycobacterium* from *Mycobacterium* The crystal violet may be provided in an amount in excess of 0.5 µg/ml.

In one aspect, there is provided a growth medium for the growth of *Mycobacterium*. The growth medium may include agar, one or more amino acid and nitrogenous supplementation elements, one or more trace elements and vitamins, one or more carbon sources, one or more neutralizing agents and crystal violet for differentiating non-*Mycobacterium* from *Mycobacterium*. The crystal violet may be provided in an amount in excess of 0.5 µg/ml.

The above description sets forth, rather broadly, a summary of one embodiment of the present invention so that the detailed description that follows may be better understood and contributions of the present invention to the art may be better appreciated. Some of the embodiments of the present invention may not include all of the features or characteristics listed in the above summary. There are, of course, additional features of the invention that will be described below and will form the subject matter of claims. In this respect, before explaining at least one preferred embodiment of the invention in detail, it is to be understood that the invention is not limited in its application to the details of the construction and to the arrangement of the components set forth in the following description or as illustrated in the drawings. The invention is capable of other embodiments and of being practiced and carried out in various ways. Also, it is to be understood that the phraseology and terminology employed herein are for the purpose of description and should not be regarded as limiting.

BRIEF DESCRIPTION OF THE DRAWINGS

FIG. 1 substantially depicts a comparison of a limited nutrient growth media and MYChrOme media on which mycobacteria have been grown in which

FIG. 2 substantially depicts a series of growth plates of different growth media and pretreatment on which mycobacteria have been grown in which

DESCRIPTION OF CERTAIN EMBODIMENTS OF THE PRESENT INVENTION

Figure 1B:
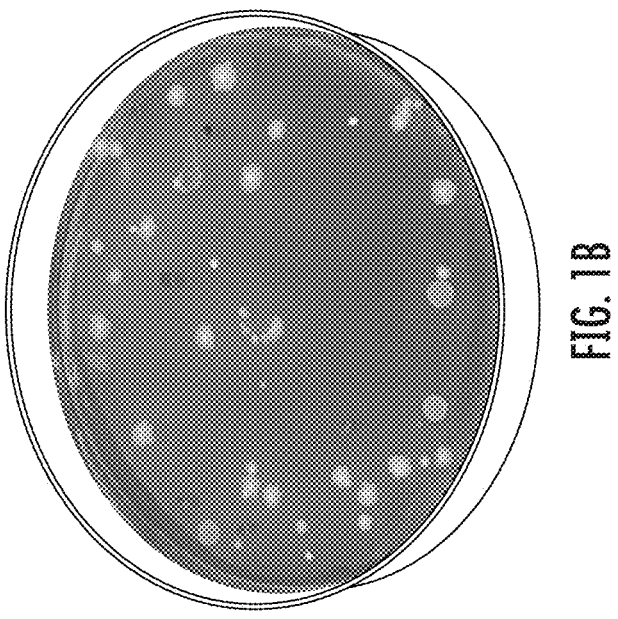
FIG. 1A shows a bacteria containing sample grown on 7H10 growth media and FIG. 1B shows the same sample plated onto MYChrOme media.

In the following detailed description of the preferred embodiments, reference is made to the accompanying drawings, which form a part of this application. The drawings show, by way of illustration, specific embodiments in which the invention may be practiced. It is to be understood that other embodiments may be utilized and structural changes may be made without departing from the scope of the present invention.

To aid the detection and differentiation of *Mycobacterium* colonies, there is provided a growth media formulation that is able to target strains of *Mycobacterium*, in particular non-tuberculosis *Mycobacterium* (NTM). For ease of reference throughout the remainder of this specification, the growing media will be referred to by the present Applicant's proprietary term MYChrOme™. The growth media formulation for MYChrOme includes a limited nutrient media containing an unusually high amount of crystal violet. Examples of the limited nutrient media include R2A, Middlebrook agar, and Plate Count Agar. Components of the nutrient media may include combinations of proteose peptone, casamino acids, yeast extract, dextrose, soluble starch, dipotassium phosphate, magnesium sulfate, sodium pyruvate, and agar. In one embodiment, the crystal violet may be added to the media in an amount of 0.5-5.0 µg/ml. In one embodiment, the concentration of crystal violet in the growing medium is at least 1.0 µg/ml. In one embodiment, the concentration of crystal violet in the growing medium is at least 1.5 µg/ml. In one embodiment, the concentration of crystal violet in the growing medium is at least 2.0 µg/ml.

In one specific example, the growth medium may contain an agar based compound. The growth medium may include one or more amino acid and nitrogenous supplementation elements, one or more trace elements and vitamins, one or more carbon sources, one or more neutralizing agents and crystal violet for differentiating non *Mycobacterium* from *Mycobacterium*.

In one embodiment, the crystal violet may be provided in an amount of 0.5-511 g/ml.

In one embodiment, the growth medium may include 0.25-1.5 g/L of proteose peptone and 0.25-1.5 g/L casamino acids to provide necessary amino acids and nitrogenous supplementation, 0.25-1.5 g/L yeast extract to boost growth and as a supply of trace elements and vitamins, 0.25-1.5 g/L dextrose as a carbon source, 0.25-1.5 g/L soluble starch as a neutralizing agent.

In addition, the growth medium may include 0.1-1.0 g/L sodium pyruvate to aid the growth of stressed microbes, 0.01-1.0 g/L magnesium sulfate and 0.1-1.0 g/L dipotassium phosphate to maintain osmotic equilibrium.

Agar may be provided as the solidifying agent in an amount of 10-20 g/L.

Bacteria-containing samples can be inoculated onto this growth media. In a liquid formulation the purple-pigmented media will turn colorless in the presence of *Mycobacterium*. In a solid formulation the media causes *Mycobacterium* to grow white colonies (or retain their original pigment) while most other bacteria grow purple colonies, allowing for rapid identification of *Mycobacterium*, especially in samples that may be heavily contaminated with competing microbiota. That *Mycobacterium* can survive with such high concentrations of crystal violet was unforeseen and unexpected. Furthermore, it was unforeseen that most other bacteria tested could not metabolize the crystal violet.

To further facilitate the identification of the *Mycobacterium*, a sample that has been obtained from the environment and filter concentrated can be treated, prior to plating, with a compound that is selective for *Mycobacterium*. In one embodiment, the treatment compound comprises a final concentration of 1-5 mM glycine hydrochloride and 0.1%-

5

1.0% sodium dodecyl sulfate (SDS). This compound, which will be referred to throughout this specification by the present Applicant's proprietary term MYCOn™, has surprisingly been found to inhibit the growth of all bacteria and fungus tested thus far other than *Mycobacterium*. MYCOn may be added to the filtered concentrate prior to plating. The benefits of MYCOn treatment have been observed with plating following immediately after treating the sample with MYCOn. In other embodiments, samples treated with MYCOn may be left to stand for a period at room temperature prior to plating. In one embodiment, the MYCOn treatment period may be at least 2 minutes. In one embodiment, the MYCOn treatment period may be at least 4 minutes. In one embodiment, the MYCOn treatment period may be at least 5 minutes. The MYCOn-treated concentrate may then be inoculated onto the MYChrOme growth medium.

Immediate plating after treatment can have the benefit of time savings, especially when processing many samples. Further, immediately plating after MYCOn treatment can eliminate potential inconsistencies from analysts not hitting the set standing period exactly every time. The step of MYCOn treatment and plating may be considered as a single step in the analysis process so that there is a consistent and repeatable process between samples. It is possible that the immediate plating of the MYCOn treatment sample may also help to reduce stress on the target *Mycobacterium* which will produce more accurate results. In one embodiment, the MYCOn treatment may be performed by an automated apparatus.

Environmental testing of approximately 318 water samples from a medical center was conducted to beta-test these diagnostics. The MYChrOme method was compared to a modified version of the ASTM E2563-07 Standard, in addition to plating on 7H10 or R2A agar. Water samples (100-200 ml) collected from each test location were filter-concentrated to 10 ml and 100 µl of the filter-concentrate was plated on both R2A or 7H10 and MYChrOme. A portion of this filter concentrate was also treated with MYCOn (SDS containing glycine hydrochloride) for five minutes, followed by plating on MYChrOme. The modified ASTM standard E2563-07 was also used to analyze each sample with plating onto 7H11 selective agar. Table 1 shows the comparison of MYChrOme detections vs. ASTM detections and demonstrates that MYChrOme is 62.8% more sensitive than the standard method.

TABLE 1

MYChrOme method vs ASTM E2563-07 method. Three hundred and eighteen (318) water samples from a healthcare facility were analyzed with the MYChrOme method and a modified ASTM E2563-07 method.

|  | MYChrOme Method | ASTM Method |
|---|---|---|
| Number of Positive Samples | 204 | 76 |
| Percent Positive | 64.2% | 23.9% |

Figure 1A:
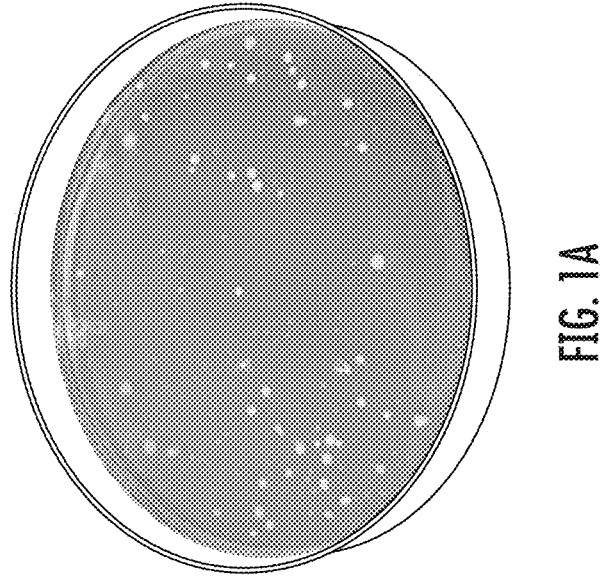

FIG. 1, comprising FIG. 1A and FIG. 1B, shows plating examples that demonstrate the benefits of the methods described herein. FIG. 1A shows a bacteria containing sample grown on 7H10 growth media. In this example, bacteria are present but different types of bacteria are indistinct from each other. That is, there was no differentiation of *Mycobacterium*, and *Mycobacterium*-positive water samples were therefore much more difficult to identify. FIG. 1B shows the sample plated onto MYChrOme media. All non-colorized colonies (mostly white colonies) were acid-fast positive and confirmed to be *Mycobacterium* on MYChrOme, while all colonies colorized by the crystal violet dye (purple) were acid-fast negative. An additional molecular screening of the aforementioned colonies by real-time Polymerase Chain Reaction confirmed the acid-fast positive colonies as *Mycobacterium* and the acid-fast negative colonies as bacteria other than *Mycobacterium*.

Figures 2A, 2B, 2C:
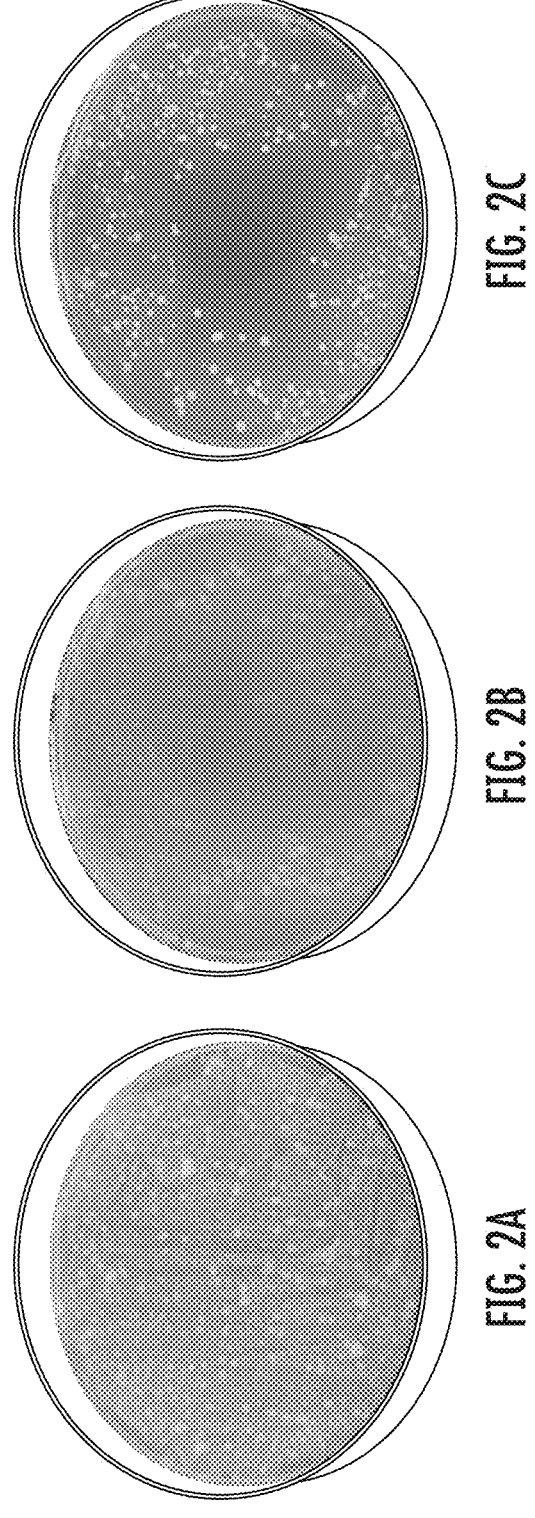
FIG. 2A shows a bacteria containing sample plated onto on 7H10 media.
FIG. 2B shows the sample plated on MYChrOme media and FIG. 2C shows the sample plated on MYChrOme media after a MYCOn pretreatment.

FIG. 2, comprising FIGS. 2A, 2B and 2C, shows comparison of a sample plated on 7H10 (FIG. 2A), MYChrOme (FIG. 2B) and MYChrOme with MYCOn pretreatment (FIG. 2C). In this example, only *Mycobacterium* species grew while all other bacterial growth was eliminated. FIG. 1 and FIG. 2 show the MYChrOme media is an optimal growth medium for identifying the presence of *Mycobacterium* and that further benefits are achieved by pre-treatment with MYCOn.

Table 2 below provides a summary of *Mycobacterium* species tested on MYChrOme. The colony color of different *Mycobacterium* species plated MYChrOme media are listed.

Table 2

TABLE 2

| | | Inclusivity organisms | | |
|---|---|---|---|---|
| Genus | Species | Source | Origin | Colony Color on MYChrOme |
| *Mycobacterium* | *abscessus* | FDA[a] 858508-1 | Not available | white |
| *Mycobacterium* | *abscessus* | FDA 923093-1075 | Not available | white |
| *Mycobacterium* | *abscessus* subsp *abscessus* | CCUG 71636[b] | Human blood | white |
| *Mycobacterium* | *abscessus* subsp. *bolletii* | CCUG 50184 | Human bronchial lavage | white |
| *Mycobacterium* | *abscessus* subsp. *massiliense* | CCUG 48898 | Human sputum | light purplish white |
| *Mycobacterium* | *agri* | CCUG 37673 | Soil | white |
| *Mycobacterium* | *aubagnense* | CCUG 50186 | Human bronchial aspirate | white |

TABLE 2-continued

Inclusivity organisms

| Genus | Species | Source | Origin | Colony Color on MYChrOme |
|---|---|---|---|---|
| *Mycobacterium* | *aurum* | CCUG 70546 | Soil | yellow |
| *Mycobacterium* | *barrassiae* | CCUG 50398 | Human bronchial lavage | white |
| *Mycobacterium* | *boenickei* | CCUG 47580 | Human wound | white |
| *Mycobacterium* | *brisbanense* | CCUG 47584 | Antral sinus | white |
| *Mycobacterium* | *canariasense* | CCUG 47953 | Human blood | white |
| *Mycobacterium* | *chelonae* | PHE[c] | Not Available | white |
| *Mycobacterium* | *chelonae* | Phigenics[d] | Env. Isolate | white |
| *Mycobacterium* | *chelonae* | CCUG 72969 | Human eye | white |
| *Mycobacterium* | *chelonae* | CCUG 37827 | Human wound | white |
| *Mycobacterium* | *chelonae* | FDA 858509-1-1-1 | Not available | white |
| *Mycobacterium* | *chelonae* | FDA 858509-2-3-2 | Not available | white |
| *Mycobacterium* | *cosmeticum* | CCUG 55442 | Human feces | white |
| *Mycobacterium* | *fortuitum* | PHE | Not Available | white |
| *Mycobacterium* | *fortuitum* | ATCC 6841 | Cold abscess | white |
| *Mycobacterium* | *fortuitum* | FDA 858508-10 | Not available | white |
| *Mycobacterium* | *fortuitum* | FDA 923093-1278 | Not available | white |
| *Mycobacterium* | *fortuitum* subsp. *fortuitum* | CCUG 46694 | Human blood | white |
| *Mycobacterium* | *franklinii* | Phigenics | Env. Isolate | white |
| *Mycobacterium* | *gadium* | CCUG 37515 | Human sputum | white |
| *Mycobacterium* | *goodii* | CCUG 5204 | Human blood | white |
| *Mycobacterium* | *hodleri* | CCUG 38151 | Chemical contaminate | white |
| *Mycobacterium* | *immunogenum* | Phigenics | Env. Isolate | white |
| *Mycobacterium* | *immunogenum* | CCUG 52935 | Water for injection | white |
| *Mycobacterium* | *iranicum* | CCUG 52297 | Human sputum | white |
| *Mycobacterium* | *mageritense* | CCUG 51275 | Human calf | white |
| *Mycobacterium* | *mucogenicum* | Phigenics | Env. Isolate | white |
| *Mycobacterium* | *mucogenicum* | FDA 858510-2 | Not available | white |
| *Mycobacterium* | *mucogenicum* | FDA 858510-4 | Not available | white |
| *Mycobacterium* | *mucogenicum* | FDA 858510-9 | Not available | white |
| *Mycobacterium* | *neoaurum* | Phigenics | Env. Isolate | yellow |
| *Mycobacterium* | *peregrinum* | CCUG 41354 | Human bronchial aspiration | white |
| *Mycobacterium* | *phocaicum* | Phigenics | Env. Isolate | white |
| *Mycobacterium* | *phocaicum* | CCUG 50185 | Human bronchial aspirate | white |
| *Mycobacterium* | *phocaicum* | FDA 858510-1 | Not available | white |
| *Mycobacterium* | *porcinum* | Phigenics | Env. Isolate | white |
| *Mycobacterium* | *porcinum* | CCUG 37674 | Swine lymph node | white |
| *Mycobacterium* | *senegalense* | CCUG 59339 | Human sputum | white |
| *Mycobacterium* | *septicum* | CCUG 47583 | Not available | white |
| *Mycobacterium* | *smegmatis* | ATCC 14468[e] | Not available | white |
| *Mycobacterium* | *wolinskyi* | CCUG 47168 | Human abscess | white |

[a]US Food and Drug Administration, Irvine, CA;

[b]CCUG-Culture Collection University of Gothenburg, Goteborg, Sweden;

[c]Public Health England, London, England;

[d]Phigenics Culture Collection, Reno, NV;

[e]American Type Culture Collection, Manassas, VA.

Table 3 below provides a summary of non-*Mycobacterium* species tested on MYChrOme. The colony color of different Non-*Mycobacterium* species plated on MYChrOme media, with and without MYCOn decontamination, are listed. Greater than $10^8$ CFU/ml of each non-*Mycobacterium* was plated.

Table 3

TABLE 3

Exclusivity organisms.

| Genus | Species | Source | Origin | Colony Color on MYChrOme Untreated | Colony Color on MYChrOme Treated |
|---|---|---|---|---|---|
| *Acinetobacter* | *baumannii* | NCIMB 12457[a] | Urine | Purple | Not Detected |
| *Aeromonas* | *hydrophila* | ATCC 35654[b] | Not Available | Purple | Not Detected |
| *Alcaligenes* | *faecalis* | ATCC 35655 | Not Available | Purple | Not Detected |
| *Bacillus* | *subtilis* | ATCC 14990 | Nose | Not Detected | Not Detected |
| *Burkholderia* | *cepacia* | ATCC 25608 | Incision wound | Purple | Not Detected |
| *Chryseobacterium* | *shigense* | ATCC 51823 | Milk | Purple | Dark purple/maroon |
| *Elizabethkingia* | *meningoseptica* | ATCC 13253 | Spinal fluid | Purple | Not Detected |
| *Escherichia* | *coli* | ATCC 10536 | Not Available | Purple | Not Detected |
| *Klebsiella* | *aerogenes* | ATCC 13048 | Sputum | Purple | Not Detected |
| *Klebsiella* | *pneumonia* | NCTC 13340[c] | Not Available | Purple | Not Detected |
| *Legionella* | *anisa* | Phigenics[d] | Env. Isolate | Not Detected | Not Detected |
| *Legionella* | *birminghamensis* | CCUG 31233 | Human lung biopsy | Purple | Not Detected |
| *Legionella* | *bozemanii* | CCUG 16416 | Lung aspirate | Not Detected | Not Detected |
| *Legionella* | *feelei* | CCUG 29668 | Human lung tissue | Dark Grey | Not Detected |
| *Legionella* | *jordansis* | CCUG 16413 | Jordan river | Not Detected | Not Detected |
| *Legionella* | *longbeachae* | ATCC 33462 | Human lung | Not Detected | Not Detected |
| *Legionella* | *pneumophila* sg 1 | CCUG 9568T | Human lung | Not Detected | Not Detected |
| *Legionella* | *pneumophila* sg 7 | ATCC 33823 | Human lung | Not Detected | Not Detected |
| *Legionella* | *sainthelensi* | CCUG 29672T | Stream Water | Not Detected | Not Detected |
| *Legionella* | *wadsworthii* | CCUG 16415T | Human sputum | Not Detected | Not Detected |
| *Methylobacterium* | spp. | Phigenics | Env. Isolate | Not Detected | Not Detected |
| *Microbacterium* | *oxydans/ maritypicum* | Phigenics | Env. Isolate | Not Detected | Not Detected |
| *Nocardia* | *brasiliensis* | ATCC 19296 | Not Available | Off White | Not Detected |
| *Pseudomonas* | *aeruginosa* | ATCC 27853 | Blood | Purple | Purple |
| *Pseudomonas* | *fragi* | ATCC 51821 | Milk | Purple | Not Detected |
| *Pseudomonas* | *mosseli* | ATCC 49838 | Not Available | Purple | Not Detected |
| *Pseudomonas* | *stutzeri* | ATCC 17588 | Spinal fluid | Purple | Not Detected |
| *Sphingomonas* | *paucimobilis* | ATCC 29837 | Hospital respirator | Purple | Not Detected |
| *Staphylococcus* | *aureus* | ATCC 25923 | Clinical | Purple | Not Detected |
| *Stenotrophomonas* | *maltophilia* | ATCC 17666 | Tissue culture | Purple | Not Detected |

[a]National Collection of Industrial, Food and Marine Bacteria, Aberdeen, Scotland;
[b]American Type Culture Collection, Manassas, VA.;
[c]National Type Culture Collection, Salisbury, England;
[d]Phigenics Culture Collection, Reno, Nevada Tables 2 and 3 demonstrate that the MYChrOme medium is useful for distinguishing many types of *Mycobacterium* from other types of bacteria.

Figure 3:
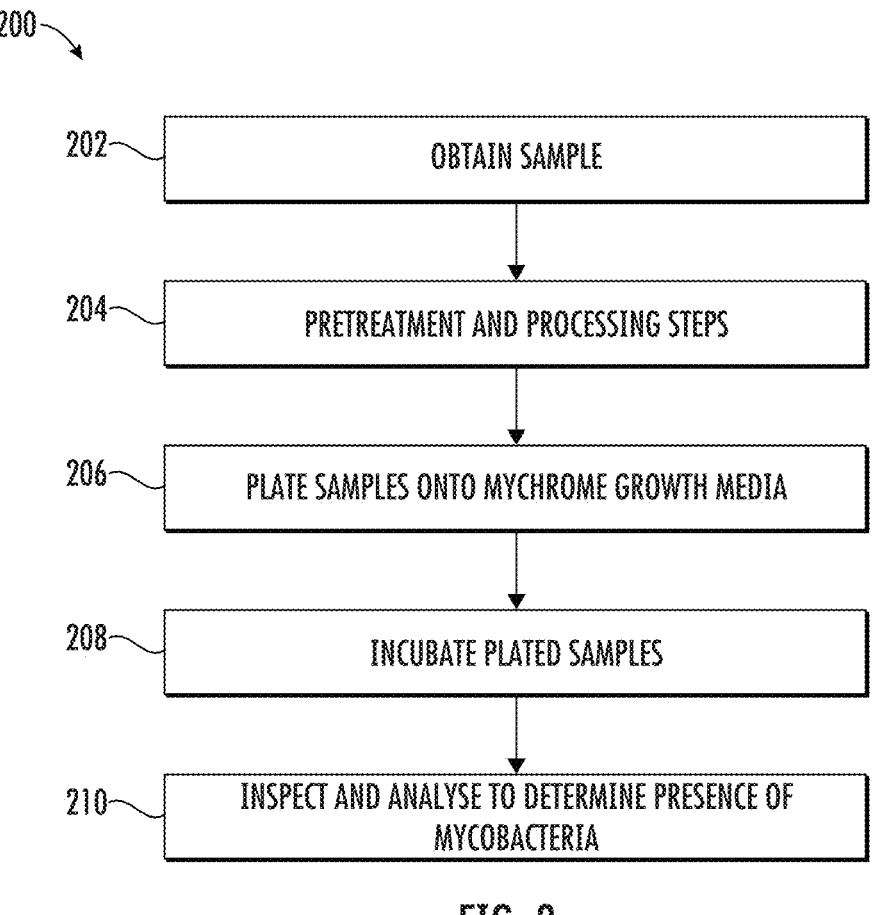
FIG. 3 substantially depicts a flowchart of a method for detecting presence of *Mycobacterium* in an environment.

FIG. 3 shows a flowchart 200 of a method for determining the presence of *Mycobacterium* in a sample. At step 202, a sample is obtained from an environment. The environment may be any environment, e.g. residential, industrial, rural, medical, etc. The environment may also be a clinical environment for testing of clinical samples. The sample may undergo preparation steps 204. For example, the sample may be filter concentrated. At step 206, the prepared sample is plated onto one or more plates of a growth media of MYChrOme. The plating process may include a dipslide process as described in the Applicant's granted patent application U.S. Pat. No. 7,901,932, the entire contents of which are incorporated herein by reference. The plated samples may be allowed to incubate for an incubation period 208. For example, the incubation period may be 1-6 weeks. An inspection 210 of the plates can then determine the presence of *Mycobacterium*. The *Mycobacterium* may be revealed as substantially white colonies on the growth media.

Figure 4:
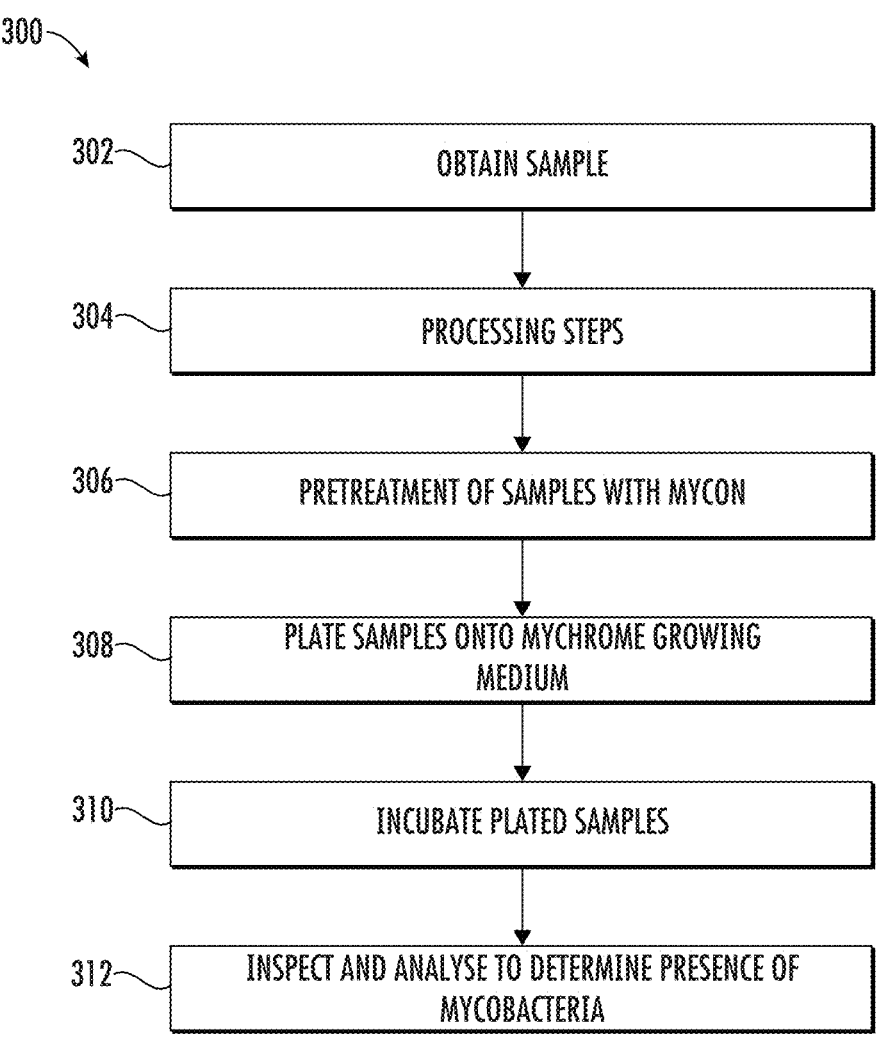
FIG. 4 substantially depicts a flowchart of an alternative method for detecting presence of *Mycobacterium* in an environment.

FIG. 4 shows a flowchart 300 of an enhanced method for determining the presence of *Mycobacterium* in a sample. At step 302, a sample is obtained from an environment. The sample may undergo one or more processing steps 304. For example, the sample may be filter concentrated. At step 306 the sample is treated with MYCOn containing sodium dodecyl sulfate containing glycine hydrochloride. At step 308, the sample is plated onto one or more plates of a growth media. The growth media may be MYChrOme though other growth media may be suitable. The growth medium is then incubated for an incubation period 310. For example, the incubation period may be 1-6 weeks. An inspection 312 of the plate(s) can then determine the presence of *Mycobacterium*.

Many modifications and other implementations of the disclosure set forth herein will come to mind to one skilled in the art to which this disclosure pertains having the benefit of the teachings presented in the foregoing descriptions and the associated drawings. Therefore, it is to be understood that the disclosure is not to be limited to the specific implementations disclosed, and that modifications and other implementations are intended to be included within the scope of the appended claims. Moreover, although the foregoing descriptions and the associated drawings describe example implementations in the context of certain example combinations of elements and/or functions, it should be appreciated that different combinations of elements and/or functions may be provided by alternative implementations without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

What is claimed is:

1. A method for determining the presence of *Mycobacterium* in a sample, comprising:

(A) obtaining a sample from an environment;

(B) treating the sample with a compound containing sodium dodecyl sulfate and glycine hydrochloride, wherein the compound comprises 1-5 mM glycine hydrochloride and 0.1%-1.0% sodium dodecyl sulfate;

(C) plating the sample treated with sodium dodecyl sulfate containing glycine hydrochloride onto a growing medium;

(D) incubating a plated sample for an incubation period; and (E) after the incubation period, inspecting one or more bacterial growth colonies to determine the presence of *Mycobacterium* in the environment.

2. The method of claim 1 comprising treating the sample with sodium dodecyl sulfate containing glycine hydrochloride for at least 4 minutes at room temperature.

3. The method of claim 1 wherein the sample is plated onto the growth medium immediately after treatment with the compound.

* * * * *